(12) United States Patent
Ehrhardt et al.

(10) Patent No.: US 7,696,184 B2
(45) Date of Patent: Apr. 13, 2010

(54) AMINO-PROPANOL DERIVATIVES AS SPHINGOSINE-1-PHOSPHATE RECEPTOR MODULATOR

(75) Inventors: Claus Ehrhardt, Lörrach (DE); Klaus Hinterding, Wittlingen (DE)

(73) Assignee: Novartis AG, Basel (CH)

( * ) Notice: Subject to any disclaimer, the term of this patent is extended or adjusted under 35 U.S.C. 154(b) by 118 days.

(21) Appl. No.: 10/558,690

(22) PCT Filed: Jun. 11, 2004

(86) PCT No.: PCT/EP2004/006318

§ 371 (c)(1), (2), (4) Date: Nov. 29, 2005

(87) PCT Pub. No.: WO2004/110979

PCT Pub. Date: Dec. 23, 2004

(65) Prior Publication Data

US 2007/0010494 A1  Jan. 11, 2007

(30) Foreign Application Priority Data

Jun. 12, 2003 (GB) ................. 0313612.4

(51) Int. Cl.
- *A61K 31/135* (2006.01)
- *A61K 31/661* (2006.01)
- *A61K 31/662* (2006.01)

(52) U.S. Cl. ................ 514/114; 514/646; 564/15; 564/374

(58) Field of Classification Search ........... 564/15, 564/347, 374
See application file for complete search history.

(56) References Cited

U.S. PATENT DOCUMENTS 5,948,820 A * 9/1999 Fujita et al. ............... 514/653

FOREIGN PATENT DOCUMENTS

| WO | 01/58889 | | 8/2001 |
| WO | 02/076995 | A2 | 10/2002 |

OTHER PUBLICATIONS

U.S. Appl. No. 10/554,556, filed Oct. 2005, Hinterding, et al.*

* cited by examiner

*Primary Examiner*—Rebecca L Anderson
*Assistant Examiner*—Shawquia Young
(74) *Attorney, Agent, or Firm*—Hoxie & Associates, LLC

(57) ABSTRACT

The present invention relates to amino-propanol derivatives, process for their production, their uses in treating and/or preventing diseases or disorders mediated by lymphocyte interactions, and pharmaceutical compositions containing them. For example, Compounds of formula I

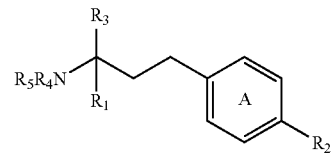

wherein A, $R_1$, $R_2$, $R_3$, $R_4$ and $R_5$ are as defined in the specification are described.

5 Claims, No Drawings

AMINO-PROPANOL DERIVATIVES AS SPHINGOSINE-1-PHOSPHATE RECEPTOR MODULATOR

The present invention relates to amino-propanol derivatives, process for their production, their uses and pharmaceutical compositions containing them.

Particularly, the invention provides a compound of formula I

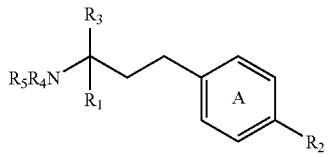

wherein $R_1$ is $C_{1-6}$alkyl; $C_{1-6}$alkyl substituted by hydroxy, $C_{1-2}$alkoxy or 1 to 6 fluorine atoms; $C_{2-6}$alkenyl; or $C_{2-6}$alkynyl;

$R_2$ is $C_{1-10}$alkyl; $C_{1-10}$haloalkyl; $C_{1-9}$alkoxy; $C_{1-9}$haloalkoxy; each optionally substituted on the terminal C atom by phenyl, phenoxy, $C_{3-6}$cycloalkyl, $C_{3-6}$cycloalkoxy, heteroaryl, heteroaryloxy, a heterocyclic residue, wherein phenyl, phenoxy, $C_{3-6}$cycloalkyl, $C_{3-6}$cycloalkoxy, heteroaryl, heteroaryloxy, a heterocyclic residue each may be ring-substituted by 1 to 5 substituents selected from hydroxy, halogen, $C_{1-4}$alkyl, $C_{1-4}$haloalkyl, $C_{3-6}$cycloalkyl, $C_{1-4}$alkoxy, $C_{1-4}$haloalkoxy, $C_{3-6}$cycloalkoxy, $C_{3-6}$cycloalkyl$C_{1-2}$alkyl, cyano, phenyl, and phenyl substituted by hydroxy, halogen, $C_{1-4}$alkyl, $C_{1-4}$haloalkyl, $C_{1-4}$alkoxy, or cyano; or a residue of the formula (b)

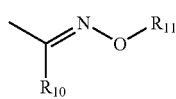

(b)

wherein $R_{10}$ is $C_{1-6}$alkyl and $R_{11}$ is $C_{1-6}$alkyl; $C_{1-10}$haloalkyl; each optionally substituted on the terminal C atom by a phenyl, phenoxy, $C_{3-6}$cycloalkyl, $C_{3-6}$cycloalkoxy, heteroaryl, heteroaryloxy, a heterocyclic residue, wherein phenyl, phenoxy, $C_{3-6}$cycloalkyl, $C_{3-6}$cycloalkoxy, heteroaryl, heteroaryloxy, a heterocyclic residue each may be ring-substituted by 1 to 5 substituents selected from, hydroxy, halogen, $C_{1-4}$alkyl, $C_{1-4}$haloalkyl, $C_{3-6}$cycloalkyl, $C_{1-4}$alkoxy, $C_{3-6}$cycloalkoxy, $C_{3-6}$cycloalkyl$C_{1-2}$alkyl, cyano, phenyl and phenyl substituted by hydroxy, halogen, $C_{1-4}$alkyl, $C_{1-4}$alkoxy, $C_{1-4}$haloalkyl or cyano;

$R_3$ is Z-$X_2$ wherein Z is $CH_2$, CHF, CHMe or $CF_2$ and $X_2$ is OH or a residue of formula (a)

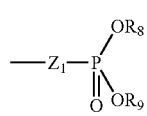

(a)

wherein $Z_1$ is a direct bond, $CH_2$, CHF, $CF_2$ or O, and each of $R_8$ and $R_9$, independently, is H or $C_{1-4}$alkyl optionally substituted by 1, 2 or 3 halogen atoms; and each of $R_4$ and $R_5$, independently, is H; $C_{1-4}$alkyl optionally substituted by 1, 2 or 3 halogen atoms; or acyl;

and ring A is substituted by $R_2$ and by two additional substituents, preferably in ortho-position to $R_2$;

in free form or in salt form.

Preferably, the two additional substituents are electrophilic substituents. The two additional substituents may be identical or different.

A preferred compound of formula I is

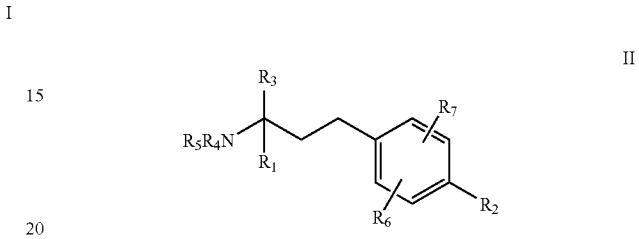

II wherein $R_1$ to $R_5$ are as defined above and each of $R_6$ and $R_7$, independently, Is hydroxy; halogen; $C_{1-4}$alkyl; $C_{1-6}$cycloalkyl; $C_{1-4}$alkoxy;

$C_{1-6}$cycloalkoxy; $C_{3-6}$cycloalkyl$C_{1-2}$alkyl; $C_{1-4}$haloalkyl; $C_{1-4}$haloalkoxy; or cyano;

in free form or in salt form.

Preferably $R_6$ and $R_7$ are in ortho-position to $R_2$.

Alkyl or alkyl moiety may be straight or branched chain. Alkenyl may be e.g. vinyl. Alkynyl may be e.g. propyn-2-yl. Acyl may be a residue R-CO wherein R is $C_{1-6}$alkyl, $C_{3-6}$cycloalkyl, phenyl or phenyl $C_{1-4}$alkyl. Halogen may be fluorine, chlorine or bromine, preferably fluorine or chlorine. When alkyl is substituted by hydroxy, it is preferably on the terminal carbon atom. Phenyl$C_{1-2}$alkyl may be e.g. benzyl. Haloalkyl may be straight chain or branched alkyl substituted by one or more halogen atoms, preferably fluorine atoms.

Heteroaryl may be a 5 to 8 membered aromatic ring comprising 1 to 4 heteroatoms selected from N, O and S, e.g. pyridyl, pyrimidinyl, pyrazinyl, furyl, oxazolyl, isoxazolyl, thienyl, thiazolyl, isothiazolyl, pyrrolyl, imidazolyl, or pyrazolyl.

By heterocyclic residue is meant a 3 to 8, preferably 5 to 8, membered saturated or unsaturated heterocyclic ring comprising e.g. tetrahydrofuryl, tetrahydropyranyl, aziridinyl, piperidinyl, pyrrolidinyl, piperazinyl.

Compounds of formula I may exist in free form or in salt form, e.g. addition salts with e.g. inorganic acids, such as hydrochloride, hydrobromide or sulfate, salts with organic acids, such as acetate, fumarate, maleate, benzoate, citrate, malate, methanesulfonate or benzenesulfonate salts. Compounds of formula I and their salts, in hydrate or solvate form are also part of the invention.

When the compounds of formula I have asymmetric centers in the molecule, various optical isomers are obtained. The present invention also encompasses enantiomers, racemates, diastereoisomers and mixtures thereof. For example, the central carbon atom bearing $R_1$, $R_3$ and $NR_4R_5$ may have the R or S configuration. Compounds of formula I having the following 3-dimensional configuration are generally preferred:

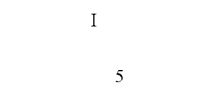

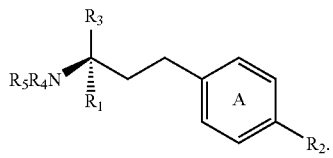

Moreover, when the compounds of formula I include geometric isomers, the present invention embraces cis-compounds, trans-compounds and mixtures thereof. Similar considerations apply in relation to starting materials exhibiting asymmetric carbon atoms or unsaturated bonds as mentioned above, e.g. compounds of formula III, IV or V as indicated below.

In the compounds of formula I, the following significances are preferred individually or in any sub-combination:
1. $R_1$ is $CH_3$ or $CH_2$—OH;
2. $R_2$ is $C_{1-7}$alkyl or $C_{1-6}$alkoxy;
4. $R_3$ is $CH_2$—OH or $CH_2$—$OPO_3H_2$;
5. each of $R_4$ and $R_5$ is hydrogen;
6. $R_6$ is methyl, methoxy, trifluoromethyl, chloro, fluoro or bromo;
7. $R_6$ is ortho to $R_2$;
8. $R_7$ is methyl, methoxy, trifluoromethyl, chloro, fluoro or bromo;
9. $R_7$ is ortho to $R_2$.

The present invention also includes a process for the preparation of compounds of formula I which process comprises a) for a compound of formula I wherein $R_3$ is $Z-X_2$, $X_2$ being OH, removing the protecting group present in a compound of formula III

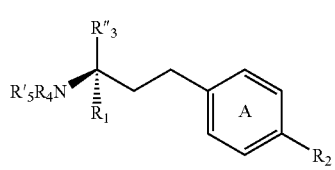

wherein X, $R_1$, $R_2$ and $R_4$ are as defined above, $R'_3$ is $Z-X_2$ wherein $X_2$ is OH, $R'_5$ is an amino protecting group, and ring A is as defined above, or b) for a compound of formula I wherein $R_3$ is $Z-X_2$, $X_2$ being a residue of formula (a), removing the protecting groups present in a compound of formula IV

wherein X, $R_1$, $R_2$, $R_4$ and $R'_5$ are as defined above, ring A is as defined above, and $R''_3$ is $Z-X_2$ wherein $X_2$ is a residue of formula (a')

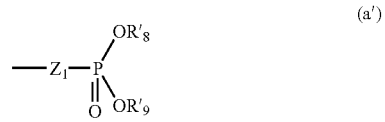

wherein $Z_1$ is as defined above and each of $R'_8$ or $R'_9$ is a hydrolysable or hydrogenolysable group or $R'_8$ and $R'_9$ form together a divalent bridging residue optionally fused to a ring (e.g. benzene ring), and, where required, converting the compounds of formula I obtained in free form into the desired salt form, or vice versa.

Process step a) may be carried out in accordance with methods known in the art. The removal of the amino protecting groups may conveniently be performed according to methods known in the art, e.g. by hydrolysis, e.g. in an acidic medium, for example using hydrochloric acid. Examples of protecting groups for amino groups are e.g. as disclosed in "Protective Groups in Organic Synthesis" T. W. Greene, J. Wiley & Sons NY, $2^{nd}$ ed., chapter 7, 1991, and references therein, e.g. benzyl, p-methoxybenzyl, methoxymethyl, tetrahydropyranyl, trialkylsilyl, acyl, tert.-butoxy-carbonyl, benzyloxycarbonyl, 9-fluorenyl methoxy carbonyl, trifluoroacetyl, and the like.

In the residue of formula (a'), each of $R'_8$ and $R'_9$ may have the significance of e.g. tert-butyl, phenyl or benzyl or form together a cyclic system such as in 1,5-dihydro-2,4,3-benzo-dioxaphosphepin.

Process step b) may be performed according to methods known in the art, e.g. by hydrolysis, e.g. in a basic medium when $R'_6$ and $R'_7$ are each a hydrolysable group, for example using a hydroxide such as barium hydroxide or in an acidic medium when $R'_6$ and $R'_7$ are each a tert-butyl group. It may also be performed by hydrogenolysis, e.g. in the presence of a catalyst, e.g. Pd/C, followed by hydrolysis, e.g. in an acidic medium, for example HCl. Compounds of formulae III and IV, used as starting materials, and salts thereof are also novel and form part of the invention.

The present invention also includes a process for the preparation of a compound of formula III which process comprises transforming a compound of formula V

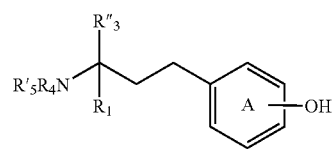

wherein $R_1$, $R'_3$, $R_4$ and $R'_5$ are as defined above, and ring A is as defined above, to introduce the desired residue —$R_2$ e.g. by an alkylation. Alkylation of the compounds of formula V may be performed according to methods known in the art, e.g. by nucleophilic substitution, e.g. by reaction with an alkylating agent $X_3$-$R_2$ wherein $X_3$ is mesylate, tosylate, triflate, nosylate, chloride, bromide or iodide. The alkylation may also be carried out by following the Mitsunobu protocol using HO—$R_2$ (e.g. as disclosed in Hughes, Organic Preparations and Procedures International 28, 127-64, 1996 or D. L. Hughes, Org. React. 42, 335, 1992), in solution or on solid phase support synthesis, e.g. by attaching the compound of formula IV to a resin. Alternatively, e.g. triphenylphosphine or diethyl azocarboxylate bound to a resin, e.g. polystyrene, may be used.

Compounds of formula IV wherein $R'_8$ and $R'_9$ form a cyclic system, may be prepared as follows:

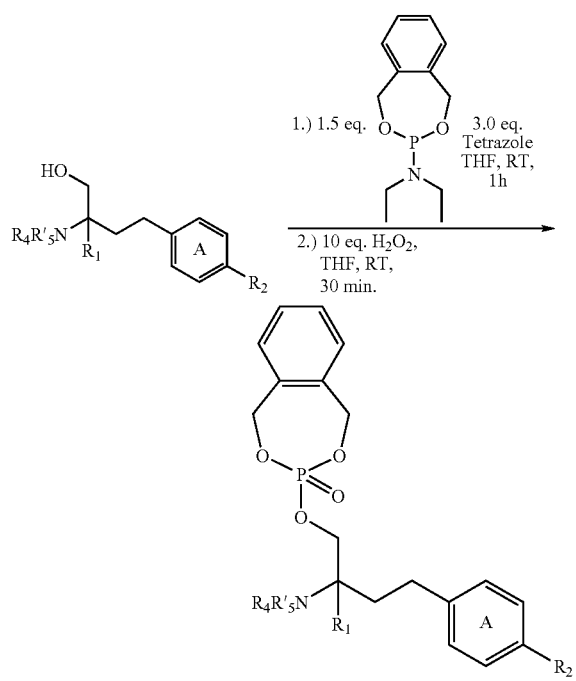

wherein X, Y, $R_1$, $R_2$, $R_4$ and $R'_5$ are as defined above, and ring A is as defined above.

Insofar as the production of the starting materials is not particularly described, the compounds are known or may be prepared analogously to methods known in the art or as disclosed in the Examples hereinafter.

The following Examples are illustrative of the invention.

| | |
|---|---|
| RT = | room temperature |
| AcOEt = | ethyl acetate |
| Et$_2$O = | diethyl ether |

EXAMPLE 1

(R)-2-Amino-4-(3,5-dichloro-4-pentyloxy-phenyl)-2-methyl-butan-1-ol Hydrotriflate

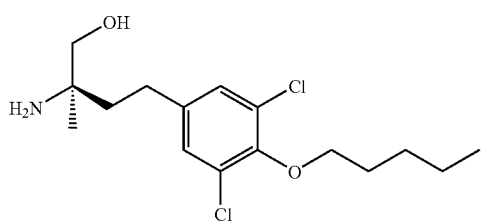

A solution of [(R)-1-Hydroxymethyl-1-methyl-3-(4-pentyloxy-phenyl)-propyl]-carbamic acid tert-butyl ester (550 mg, 1.50 mmol) in acetic acid (20 ml), conc. HCl (0.625 ml) and H$_2$O$_2$ (30%, 0.17 ml) is stirred at 45° C. for 2 h. After evaporation of the solvent, the oily residue is purified first by chromatography on silica gel using AcOEt/methanol=85/15 and second by reverse phase preparative HPLC (20×250 mm, RP18: 10 μm) using acetonitrile/water/trifluoroacetic acid=900/100/1 as eluent to yield the title compound as white solid.

MS (ESI+): m/z=334/336 (MH$^+$).

EXAMPLE 2

(R)-2-Amino-4-(3-bromo-5-methyl-4-pentyloxy-phenyl)-2-methyl-butan-1-ol Hydrotriflate

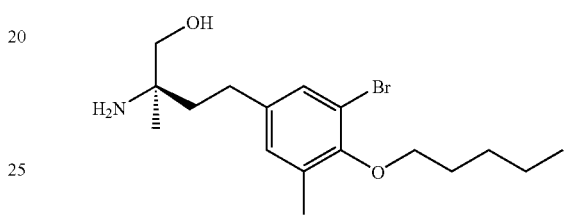

To a solution of (R)-4-[2-(3-Bromo-5-methyl-4-pentyloxy-phenyl)-ethyl]-4-methyl-oxazolidin-2-one (58 mg, 0.15 mmol) in ethanol (2 ml) is added a solution of LiOH-hydrate (180 mg, 4.28 mmol) in water (1.5 ml). The mixture is stirred at 90° C. for 2 h. After cooling to RT and extraction with AcOEt (2×20 ml), the organic phase is dried using MgSO$_4$. Evaporation of solvent is followed by reverse phase preparative HPLC (20×250 mm, RP18: 10 μm) using acetonitrile/water/trifluoroacetic acid=900/100/1 as eluent to yield the title compound as white solid. MS (ESI+): m/z=358/360 (MH$^+$).

EXAMPLE 3

(R)-2-Amino-4-(3,5-dibromo-4-pentyloxy-phenyl)-2-methyl-butan-1-ol Hydrochloride

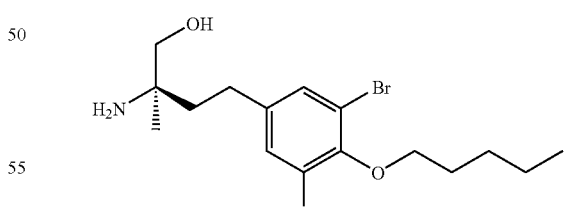

To a solution of (R)-4-[2-(3,5-Dibromo-4-pentyloxy-phenyl)-ethyl]-4-methyl-oxazolidin-2-one (45 mg, 0.10 mmol) in ethanol (2 ml) is added a solution of LiOH-hydrate (180 mg, 4.28 mmol) in water (1.5 ml). The mixture is stirred at 90° C. for 2 h. After cooling to RT and extraction with AcOEt (2×20 ml), the organic phase is dried using MgSO$_4$. Evaporation of solvent is followed by addition of 1 M HCl (0.2 ml). The product is dissolved in MeOH (0.5 ml) and precipitated by addition of Et$_2$O (10 ml) to yield the title compound as white solid. MS (ESI+): m/z=422/424/426 (MH$^+$).

EXAMPLE 4

Phosphoric acid mono-[(R)-2-amino-4-(3,5-dichloro-4-pentyloxy-phenyl)-2-methyl-butyl]ester

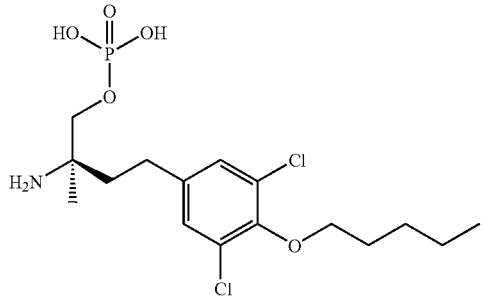

A solution of [(R)-1-(Di-tert-butoxy-phosphoryloxymethyl)-3-(3,5-dichloro-4-pentyloxy-phenyl)-1-methyl-propyl]-carbamic acid tert-butyl ester (43 mg, 0.07 mmol) in acetic acid (0.4 ml) and conc. HCl (0.042 ml) is left standing at RT for 4 h. After evaporation of the solvent, the oily residue is treated with Et$_2$O to yield the title compound as a white precipitate which is filtered off. MS (ESI−): m/z =413/415 (M−H$^−$).

EXAMPLE 5

(R)-2-Amino-4-[3-chloro-5-methoxy-4-(4,4,5,5,5-pentafluoro-pentyloxy)-phenyl]-2-methyl-butan-1-ol Hydrochloride

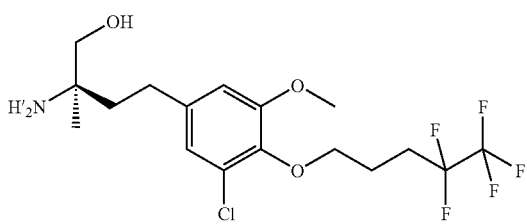

A solution of {(R)-1-Hydroxymethyl-3-[3-methoxy-4-(4,4,5,5,5-pentafluoro-pentyloxy)-phenyl]-1-methyl-propyl}-carbamic acid tert-butyl ester (32 mg, 0.07 mmol) in acetic acid (1 ml), conc. HCl (0.027 ml) and H$_2$O$_2$ (30%, 0.074 ml) is stirred at RT for 2 h. After evaporation of the solvent at RT, the oily residue is treated with toluene (1 ml), which is distilled off at RT. Et$_2$O is added and the white precipitate is filtered off to yield the title compound. MS (ESI+): m/z=420/422 (MH$^+$).

EXAMPLE 6

Phosphoric acid mono-{(R)-2-amino-4-[3-chloro-5-methoxy-4-(4,4,5,5,5-pentafluoro-pentyloxy)-phenyl]-2-methyl-butyl}ester

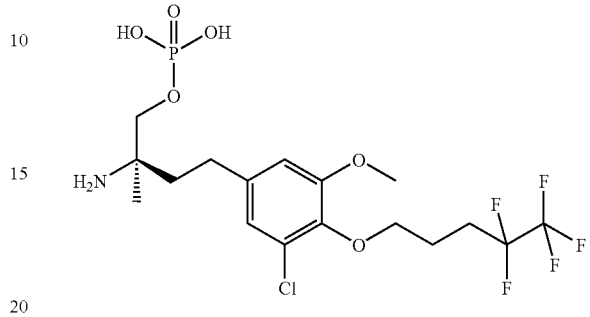

The title compound is prepared according to ex. 4 using [(R)-3-[3-chloro-5-methoxy-4-(4,4,5,5,5-pentafluoro-pentyloxy)-phenyl]-1-(di-tert-butoxy-phosphoryloxymethyl)-1-methyl-propyl]-carbamic acid tert-butyl ester as starting material. MS (ESI−): m/z=498 (M−H$^−$).

EXAMPLE 7

(R)-2-Amino-4-(3-chloro-5-fluoro-4-pentyloxy-phenyl)-2-methyl-butan-1-ol Hydrochloride

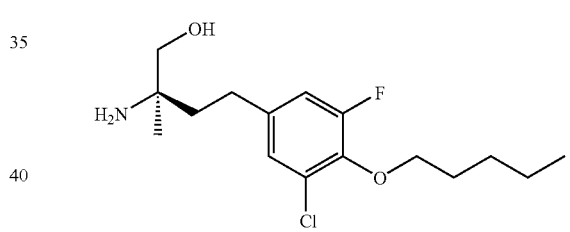

[(R)-3-(3-Chloro-5-fluoro-4-pentyloxy-phenyl)-1-hydroxymethyl-1-methyl-propyl]-carbamic acid tert-butyl ester (10 mg) is dissolved in dioxane containing 4 M HCl (0.5 ml). After stirring at RT for 18 h the product is precipitated by the addition of Et$_2$O to yield the title compound as white solid. MS (ESI+): m/z=319 (MH$^+$).

EXAMPLE 8

(R)-2-Amino-4-(3-chloro-5-methoxy-4-pentyloxy-phenyl)-2-methyl-butan-1-ol Hydrotriflate

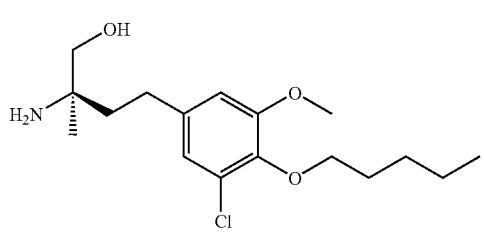

The title compound is prepared according to ex. 7 using [(R)-3-(3-Chloro-5-methoxy-4-pentyloxy-phenyl)-1-hydroxymethyl-1-methyl-propyl]-carbamic acid tert-butyl ester as starting material. The crude product is purified by reverse phase preparative HPLC (20×250 mm, RP18: 10 μm) using acetonitrile/water/trifluoroacetic acid=900/100/1 as eluent to yield the title compound as white solid. MS (ESI+): m/z=331 (MH+).

EXAMPLE 9

(R-2-Amino-4-{3-chloro-4-[2-(4-ethoxy-phenyl)-ethoxy]-5-methoxy-phenyl}-2-methyl-butan-1-ol Hydrotriflate

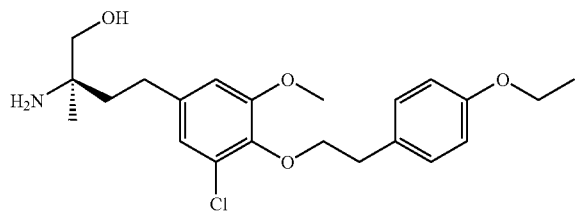

The title compound is prepared according to example 8 using ((R)-3-{3-Chloro-4-[2-(4-ethoxy-phenyl)-ethoxy]-5-ethoxy-phenyl}-1-hydroxymethyl-1-methyl-propyl)-carbamic acid tert-butyl ester as starting material. MS (ESI+): m/z=409 (MH+).

EXAMPLE 10

Phosphoric acid mono-((R)-2-amino-4-{3-chloro-4-[2-(4-ethoxy-phenyl)-ethoxy]-5-methoxy-phenyl}-2-methyl-butyl)ester

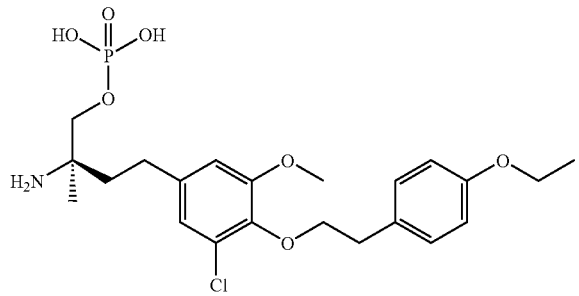

The title compound is prepared according to ex. 4 using [(R)-3-{3-chloro-4-[2-(4-ethoxy-phenyl)-ethoxy]-5-methoxy-phenyl}-1-(di-tert-butoxy-phosphoryloxymethyl)-1-methyl-propyl]-carbamic acid tert-butyl ester as starting material. MS (ESI-): m/z=487 (M-H-).

EXAMPLE 11

(R)-2-Amino-4-[4-(2-biphenyl-4-yl-ethoxy)-3-chloro-5-methoxy-phenyl]-2-methyl-butan-1-ol Hydrotriflate

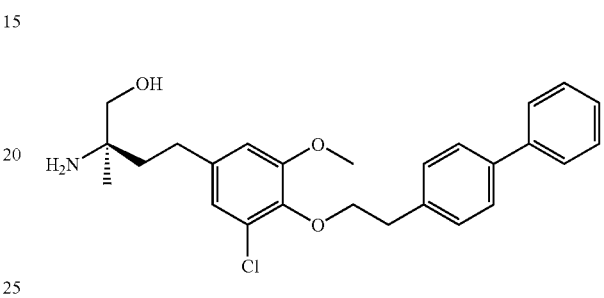

The title compound is prepared according to ex. 8 using {(R)-3-[4-(2-biphenyl-4-yl-ethoxy)-3-chloro-5-methoxy-phenyl]-1-hydroxymethyl-1-methyl-propyl}-carbamic acid tert-butyl ester as starting material. MS (ESI+): m/z=441 (MH+).

Sphingosine-1-phosphate (S1P) Receptor Profiling

Agonist activities of compounds are tested on the human SIP receptors EDG-1 ($S1P_1$), EDG-3 ($S1P_3$), EDG-5 ($S1P_2$), EDG-6 ($S1P_4$) and EDG-8 ($S1P_5$). Functional receptor activation is assessed by quantifying compound induced GTP [$\gamma$-$^{35}$S] binding to membrane protein prepared from transfected CHO or RH7777 cells stably expressing the appropriate human S1P receptor. The assay technology used is SPA (scintillation proximity based assay). Briefly, DMSO dissolved compounds are serially diluted and added to SPA-bead (Amersham-Pharmacia) immobilised S1P receptor expressing membrane protein (10-20 μg/well) in the presence of 50 mM Hepes, 100 mM NaCl, 10 mM $MgCl_2$, 10 μM GDP, 0.1% fat free BSA and 0.2 nM GTP [$\gamma$-$^{35}$S] (1200 Ci/mmol). After incubation in 96 well microtiterplates at RT for 120 min, unbound GTP [$\gamma$-$^{35}$S] is separated by a centrifugation step. Luminescence of SPA beads triggered by membrane bound GTP [$\gamma$-$^{35}$S] is quantified with a TOPcount plate reader (Packard). $EC_{50}$s are calculated using standard curve fitting software.

| Example | $S1P_1$ $EC_{50}$ [nM] | $S1P_2$ $EC_{50}$ [nM] | $S1P_3$ $EC_{50}$ [nM] | $S1P_4$ $EC_{50}$ [nM] | $S1P_5$ $EC_{50}$ [nM] |
|---|---|---|---|---|---|
| 4 | 0.2 Agon. | >10000 — | >10000 — | 0.2 Agon. | 0.2 Agon. |
| 6 | 1.3 Agon. | >10000 — | >10000 — | 0.8 Agon. | 0.2 Agon. |
| 10 | 0.3 Agon. | >10000 — | 111 — | >10000 — | 2.5 Agon. |

B. In vivo: Blood Lymphocyte Depletion

A compound of formula I or the vehicle is administered orally by gavage to rats. Tail blood for hematological monitoring is obtained on day -1 to give the baseline individual values, and at 2, 6, 24, 48 and 72 hours after application. In this assay, the compounds of formula I deplete peripheral blood lymphocytes when administered at a dose of 0.03 to 3 mg/kg. For example, following results are obtained: depletion of peripheral blood lymphocytes by more than 50%

Example 1: 0.5 mg/kg p.o. after 6 h, >1 mg/kg p.o. after 48 h.

Example 5: 0.2 mg/kg p.o. after 6 h, >1 mg/kg p.o. after 48 h.

Example 9: 0.2 mg/kg p.o. after 6 h.

The compounds of formula I are, therefore, useful in the treatment and/or prevention of diseases or disorders mediated by lymphocytes interactions, e.g. in transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others, allergic diseases, e.g. allergic asthma, atopic dermatitis, allergic rhinitis/conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis, ischemia/reperfusion injury, e.g. myocardial infarction, stroke, gut ischemia, renal failure or hemorrhage shock, traumatic shock, cancer, e.g. breast cancer, T cell lymphomas or T cell leukemias, angiogenesis, infectious diseases, e.g. toxic shock (e.g. superantigen induced), septic shock, adult respiratory distress syndrome or viral infections, e.g. AIDS, viral hepatitis, chronic bacterial infection, or senile dementia. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus. For the above uses the required dosage will of course vary depending on the mode of administration, the particular condition to be treated and the effect desired.

In general, satisfactory results are indicated to be obtained 'systemically at daily dosages of from about 0.03 to 2.5 mg/kg per body weight. An indicated daily dosage in the larger mammal, e.g. humans, is in the range from about 0.5 mg to about 100 mg, conveniently administered, for example, in divided doses up to four times a day or :in retard form. Suitable unit dosage forms for oral administration comprise from ca. 0.1 to 50 mg active ingredient.

The compounds of formula I, e.g. of formula II, may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, or in a nasal or a suppository form. Pharmaceutical compositions comprising a compound of formula I, e.g. of formula II, in free form or in pharmaceutically acceptable salt form in association with at least one pharmaceutical acceptable carrier or diluent may be manufactured in conventional manner by mixing with a pharmaceutically acceptable carrier or diluent.

The compounds of formula I, e.g. of formula II, may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by lymphocytes, e.g. such as indicated above, in a subject in need of such treatment, which method comprises administering to said subject an effective amount of a compound of formula I or a pharmaceutically acceptable salt thereof;

1.2 A method for preventing or treating acute or chronic transplant rejection or T-cell mediated inflammatory or autoimmune diseases, e.g. as indicated above, in a subject in need of such treatment, which method comprises administering to said subject an effective amount of a compound of formula I or a pharmaceutically acceptable salt thereof;

2. A compound of formula I, in free form or in a pharmaceutically acceptable salt form for use as a pharmaceutical, e.g. in any of the methods as indicated under 1.1 or 1.2 above.

3. A pharmaceutical composition, e.g. for use in any of the methods as in 1.1 or 1.2 above comprising a compound of formula I, e.g. of formula II, in free form or pharmaceutically acceptable salt form in association with a pharmaceutically acceptable diluent or carrier therefor.

4. A compound of formula I, e.g. of formula II, or a pharmaceutically acceptable salt thereof for use in the preparation of a pharmaceutical composition for use in any of the method as in 1.1 or 1.2 above.

The compounds of formula I may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g a malignant cell anti-proliferative agent. For example, the compounds of formula I, e.g. of formula II, may be used in combination with a calcineurin Inhibitor, e.g. cyclosporin A, FK 506 or ISA$_{TX}$247; a mTOR inhibitor, e.g. rapamycin, 40-O-(2-hydroxyethyl)rapamycin, CCI779, ABT578, AP23573, AP23464, AP23675, AP23841, TAFA-93, biolimus 7 or biolimus 9; an ascomycin having immuno-suppressive properties, e.g. ABT-281, ASM981, etc.; a S1P receptor agaonist e.g. FTY720 or an analogue thereof; corticosteroids; cyclophosphamide; azathioprene; methotrexate; leflunomide; mizoribine; mycophenolic acid; mycophenolate mofetil; 15-deoxyspergualine or an immunosuppressive homologue, analogue or derivative thereof; immunosuppressive monoclonal antibodies, e.g., monoclonal antibodies to leukocyte receptors, e.g., MHC, CD2, CD3, CD4, CD7, CD8, CD25, CD28, CD40. CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil; or an anti-infectious agent.

Where the compounds of formula I are administered in conjunction with other immuno-suppressive/immunomodulatory, anti-inflammatory chemotherapeutic or anti-infectious therapy, dosages of the co-administered immunosuppressant, immunomodulatory, anti-inflammatory, chemotherapeutic or anti-infectious compound will of course vary depending on the type of co-drug employed, e.g. whether it is a steroid or a calcineurin inhibitor, on the specific drug employed, on the condition being treated and so forth. In accordance with the foregoing the present invention provides in a yet further aspect:

5. A method as defined above comprising co-administration, e.g. concomitantly or in sequence, of a therapeutically effective non-toxic amount of a compound of formula I and at least a second drug substance, e.g. an immunosuppressant, immuno-modulatory, anti-inflammatory or chemotherapeutic drug, e.g. as indicated above.

6. A pharmaceutical combination, e.g. a kit, comprising a) a first agent which is a compound of formula I as disclosed herein, in free form or in pharmaceutically acceptable salt form, and b) at least one co-agent, e.g. an immunosuppressant, immunomodulatory, anti-inflammatory, chemotherapeutic or anti-infectious agent. The kit may comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula I and a co-agent, are both administered to a patient simultaneously in the form of a single entity or dosage. The term "non-fixed combination" means that the active ingredients, e.g. a compound of formula I and a co-agent, are both administered to a patent as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The invention claimed is:
1. A compound of formula II:

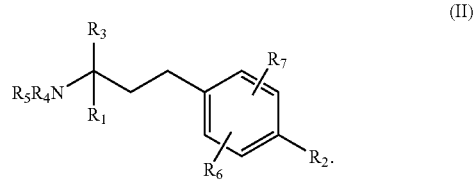

(II)

wherein $R_1$ is $C_{1-6}$-alkyl; $C_{1-6}$-alkyl substituted by hydroxy, $C_{1-2}$-alkoxy or 1-to-6 fluorine atoms; $C_{2-6}$-alkenyl; or $C_{2-6}$-alkynyl;

$R_2$ is $C_{1-9}$-alkoxy or $C_{1-9}$-haloalkoxy, where each may be optionally substituted on the terminal C atom by phenyl, phenoxy, $C_{3-6}$-cycloalkyl, $C_{3-6}$-cycloalkoxy, wherein each of phenyl, phenoxy, $C_{3-6}$-cycloalkyl and $C_{3-6}$-cycloalkoxy may be ring-substituted by 1-to-5 substituents selected from hydroxy, fluoro, chloro, bromo, $C_{1-4}$-alkyl, $C_{1-4}$-haloalkyl, $C_{3-6}$-cycloalkyl, $C_{1-4}$-alkoxy, $C_{3-6}$-cycloalkoxy, $C_{3-6}$-cycloalkyl$C_{1-2}$-alkyl, cyano, phenyl, and phenyl substituted by hydroxy, fluoro, chloro, bromo, $C_{1-4}$-alkyl, $C_{1-4}$-haloalkyl, $C_{1-4}$-alkoxy, or cyano;

$R_3$ is $Z$-$X_2$, wherein $Z$ is $CH_2$, CHF, CHMe or $CF_2$, and $X_2$ is OH or a residue of formula (a):

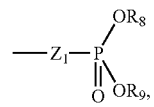

wherein $Z_1$ is a direct bond, $CH_2$, CHF, $CF_2$ or O, and each of $R_8$ and $R_9$, independently, is H or $C_{1-4}$-alkyl optionally substituted by 1, 2 or 3 fluoro, chloro and/or bromo atoms; and each of $R_4$ and $R_5$, independently, is H; $C_{1-4}$-alkyl optionally substituted by 1, 2 or 3 fluoro, chloro and/or bromo atoms; or acyl;

$R_6$ is chloro, fluoro, bromo, trifluoromethyl, methoxy or methyl; and $R_7$ is chloro, fluoro, bromo or trifluoromethyl;

in free form or in salt form.

2. A compound according to claim 1, wherein $R_2$ is $C_{1-6}$-alkoxy.

3. A pharmaceutical composition comprising a compound according to claim 1, or a pharmaceutically-acceptable salt thereof in association with a pharmaceutically-acceptable diluent or carrier therefor.

4. A pharmaceutical combination comprising a compound according to claim 1, in free form or in pharmaceutically-acceptable salt form, and at least one co-agent that is an immunosuppressive agent, an immunomodulatory agent, an anti-inflammatory agent, a chemotherapeutic agent, or an anti-infective agent.

5. A compound according to claim 1, wherein $R_6$ is methyl, trifluoromethyl, chloro or bromo; and $R_7$ is trifluoromethyl, chloro or bromo.

* * * * *